United States Patent
Miles et al.

(10) Patent No.: US 9,247,831 B2
(45) Date of Patent: Feb. 2, 2016

(54) SLEEP SURFACE INSERT SYSTEM AND METHOD THEREOF

(71) Applicants: Scott D. Miles, Sandy, UT (US); Dana L. Miles, Sandy, UT (US)

(72) Inventors: Scott D. Miles, Sandy, UT (US); Dana L. Miles, Sandy, UT (US)

( * ) Notice: Subject to any disclaimer, the term of this patent is extended or adjusted under 35 U.S.C. 154(b) by 0 days.

(21) Appl. No.: 13/907,781

(22) Filed: May 31, 2013

(65) Prior Publication Data

US 2013/0326811 A1    Dec. 12, 2013

Related U.S. Application Data

(60) Provisional application No. 61/654,678, filed on Jun. 1, 2012.

(51) Int. Cl.
| | |
|---|---|
| A47D 15/00 | (2006.01) |
| A47C 7/74 | (2006.01) |
| A47C 21/04 | (2006.01) |
| A47D 9/00 | (2006.01) |

(52) U.S. Cl.
CPC ............. *A47D 15/001* (2013.01); *A47C 7/744* (2013.01); *A47C 21/04* (2013.01); *A47C 21/044* (2013.01); *A47D 9/00* (2013.01)

(58) Field of Classification Search
CPC ............ A47C 21/04–21/05; A47C 7/74–7/744
USPC ...................... 5/726, 423, 724, 725, 284, 421
See application file for complete search history.

(56) References Cited

U.S. PATENT DOCUMENTS

| | | | |
|---|---|---|---|
| 2,462,984 A | 3/1949 | Maddison | |
| 4,777,802 A | 10/1988 | Feher | |
| 5,305,483 A | 4/1994 | Watkins | |
| 5,317,767 A | 6/1994 | Hargest et al. | |
| 5,367,728 A | 11/1994 | Chang | |
| 5,483,711 A | 1/1996 | Hargest et al. | |
| 5,509,154 A * | 4/1996 | Shafer et al. ...................... 5/713 |
| 5,787,534 A | 8/1998 | Hargest et al. | |
| 5,887,304 A | 3/1999 | von der Heyde | |
| 6,052,853 A | 4/2000 | Schmid | |
| 6,223,539 B1 | 5/2001 | Bell | |
| 6,334,228 B1 | 1/2002 | Schmid | |
| 6,336,237 B1 | 1/2002 | Schmid | |
| 6,370,718 B1 * | 4/2002 | Schmid ........................... 5/726 |
| 6,684,437 B2 | 2/2004 | Koenig | |
| 7,127,763 B1 | 10/2006 | Schmid et al. | |
| 7,656,299 B2 | 2/2010 | Gentry et al. | |
| 7,708,338 B2 | 5/2010 | Wolas | |
| 7,996,936 B2 | 8/2011 | Marquette et al. | |
| 8,065,763 B2 | 11/2011 | Brykalski et al. | |
| 8,143,554 B2 | 3/2012 | Lofy | |
| 8,181,290 B2 | 5/2012 | Brykalski et al. | |
| 8,191,187 B2 | 6/2012 | Brykalski et al. | |

(Continued)

*Primary Examiner* — Peter M Cuomo
*Assistant Examiner* — Brittany Wilson
(74) *Attorney, Agent, or Firm* — David L. Stott

(57) ABSTRACT

A sleep surface insert system and method for positioning under, for example, an infant on a sleep surface. The sleep surface insert system includes an insert and a blower system. The insert includes a top liner and a bottom liner. The top liner and bottom liner define first and a second hollow spaces therebetween. Further, the top liner includes first and second pores such that the first pores extend through the top liner from the first hollow space and the second pores extend through the top liner from the second hollow space. In addition, the blower system is configured to provide air flow into the first and second hollow spaces defined in the insert such that the air flow is configured to flow into the insert and out of at least one of the first pores and the second pores.

22 Claims, 5 Drawing Sheets

FIG. 1A

(56) References Cited

U.S. PATENT DOCUMENTS

| | | |
|---|---|---|
| 8,332,975 B2 | 12/2012 | Brykalski et al. |
| 8,418,286 B2 | 4/2013 | Brykalski et al. |
| 2005/0190068 A1 | 9/2005 | Gentry et al. |
| 2010/0011502 A1 | 1/2010 | Brykalski et al. |

* cited by examiner

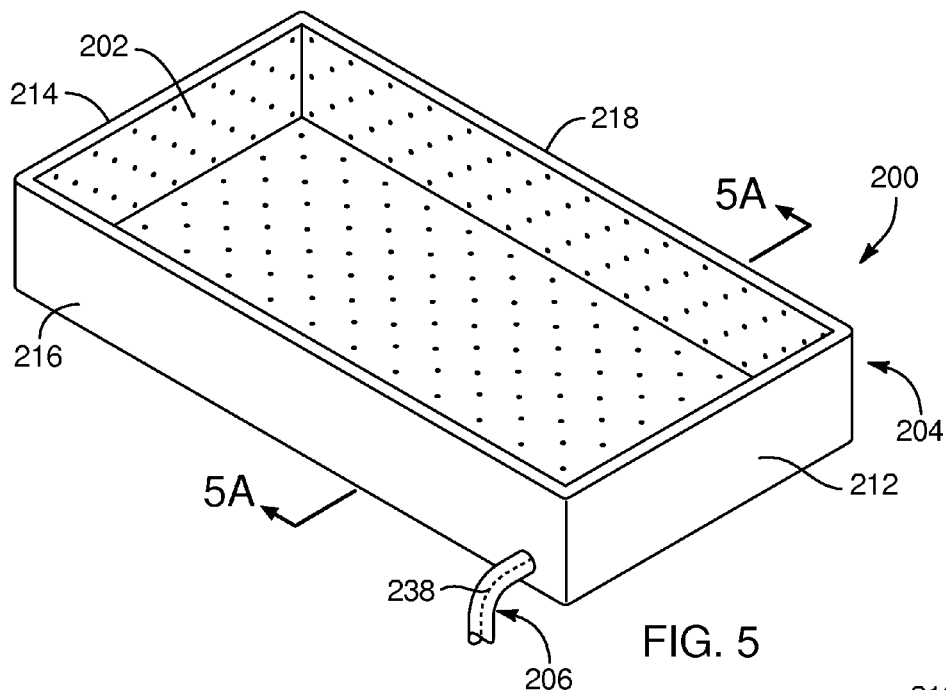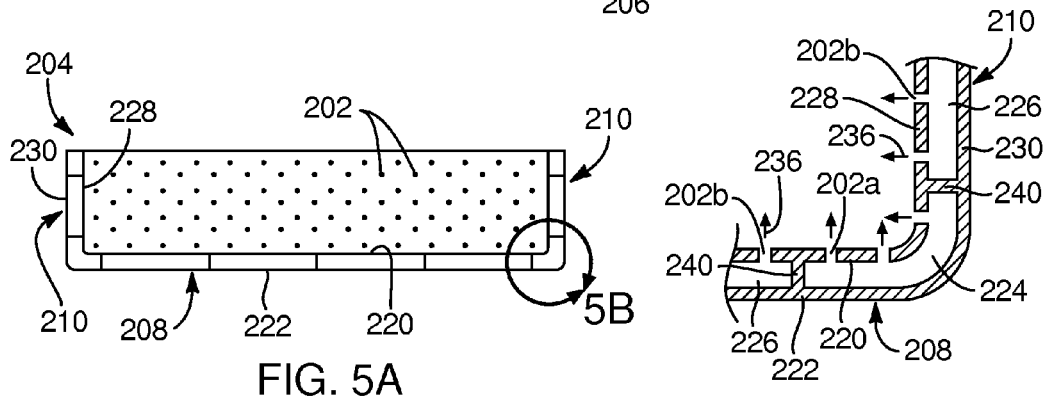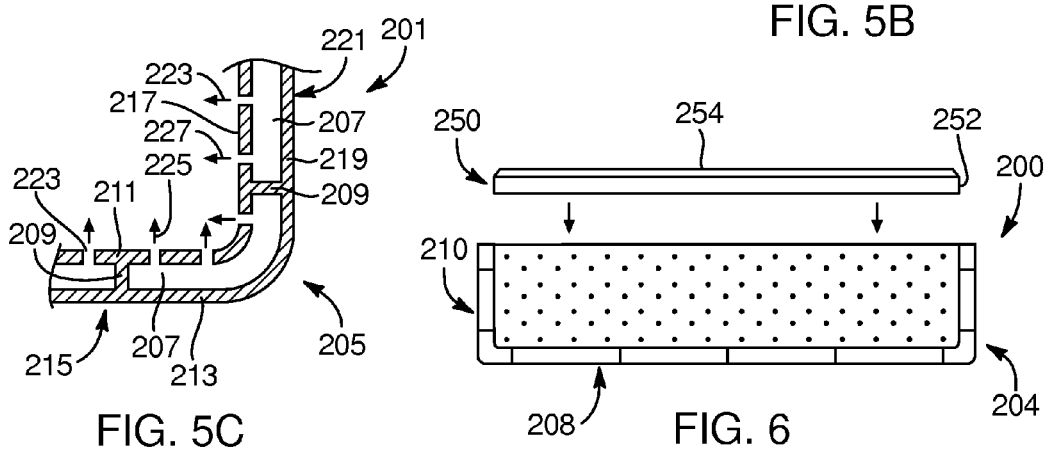

SLEEP SURFACE INSERT SYSTEM AND METHOD THEREOF

CROSS-REFERENCE TO RELATED APPLICATION

The present application claims the benefit of U.S. Provisional Patent Application Ser. No. 61/654,678, filed Jun. 1, 2012, entitled SLEEP SURFACE INSERT SYSTEM AND METHOD THEREOF, the disclosure of which is incorporated by reference herein in its entirety.

TECHNICAL FIELD

The present invention relates generally to a sleep system and method and, more specifically, the present invention relates to a sleep surface system and method for substantially preventing the conditions that lead to Sudden Infant Death Syndrome ("SIDS").

BACKGROUND

Each year, thousands of infants (aged 2 weeks to 1 year) die from Sudden Infant Death Syndrome ("SIDS"), a disorder in which otherwise healthy infants seemingly stop breathing. Although scientific and medical research has uncovered factors which indicate a predisposition to the disorder (e.g., low birth weight, age of mothers), no specific cause has been uncovered. Moreover, there are varied theories put forth by the medical community as to the cause of SIDS. Some theories suggest a neurological disorder in the infants which intercepts the breathing functions while sleeping and leads to the infant's death by asphyxiation.

Applicant believes a contributing cause of SIDS is that infants fall victim to asphyxiation from carbon dioxide re-breathing. More specifically, infants sleeping face down re-breathe the carbon dioxide in the exhaled air trapped in the air pocket of their bedding near their air passages. Doctors, nurses and medical journals have for years recommended placing an infant on its back for sleeping to avoid this concern. However, many parents and caregivers are reluctant to follow this advice. Some infants prefer sleeping on their stomachs, and do not adjust to the changed position well. Moreover after 5-6 months, most infants can roll themselves over to their preferred sleeping position. Further, many infants have a tendency to regurgitate and parents are concerned their infant may choke on the regurgitated matter.

Based on the foregoing, it would be advantageous to provide a sleep surface that will substantially prevent the conditions which can lead to carbon dioxide poisoning to infants sleeping face down and, thereby, substantially prevent SIDS.

BRIEF SUMMARY OF THE INVENTION

The present invention is directed to a sleep surface insert system for positioning under an infant on a sleep surface. In accordance with one embodiment, the sleep surface insert system includes an insert, a blower, and an actuator. The insert is configured to be placed on the sleep surface. Further, the insert includes a substantially flat configuration with a top liner having an exterior surface and a bottom liner. The top liner and bottom liner defines a first hollow space and second hollow space therebetween. The top liner includes first multiple pores and a second multiple pores, the first multiple pores extending between the first hollow space and the exterior surface of the top liner and the second multiple pores extending between the second hollow space and the exterior surface of the top liner. The blower is configured to provide air flow into the first hollow space and the second hollow space defined in the insert, the air flow configured to flow into the insert and out of at least one of the first multiple pores and the second multiple pores. The actuator is configured to alternate inflation of the insert between the first hollow space and the second hollow space defined therein.

In one embodiment, the actuator includes a solenoid. In another embodiment, the actuator is configured to actuate with a predetermined frequency. In still another embodiment, the actuator comprises a sensor, the actuator being configured to actuate upon sensing a predetermined pressure. In yet another embodiment, the actuator includes a bladder controlled diverter.

In another embodiment, the sleep surface insert system includes a sensor, controller and a thermal element configured to control a temperature of the air being blown through the insert. In still another embodiment, the sleep surface insert system includes a filter configured to filter the air being blown through the insert.

In accordance with another embodiment of the present invention, a method of Substantially eliminating risk factors which lead to sudden infant death syndrome is provided. The method includes positioning an insert on a sleep surface such that the insert includes a top liner and bottom liner that defines a first hollow space and a second hollow space therebetween, the top liner including first multiple pores and a second multiple pores corresponding with the first and second hollow spaced defined in the insert, respectively. The method also includes blowing air into the insert and through the first multiple pores and the second multiple pores such that the air is directed in an alternating manner between the first hollow space and the second hollow space to inflate the insert between the first hollow space and the second hollow space of the insert.

In another embodiment, the method step of blowing includes inflating portions of the insert corresponding with the first hollow space and the second hollow space to cause movement in a surface of the insert to jostle or rock an infant laying over the surface. In still another embodiment, the method step of blowing includes filtering the air flowing into and out of the first and second multiple pores of the insert for the infant. In another embodiment, the method step of blowing includes directing the air between the first hollow space and second hollow space with the actuator. In another embodiment, the directing step includes alternating air flow between the first hollow space and the second hollow space by sensing a predetermined air pressure in the insert. In still another embodiment, the directing step includes directing the air between the first hollow space and the second hollow space with a bladder controlled diverter.

In one embodiment, the method further includes monitoring at least one of the heart rate and respiration of the infant. In another embodiment, the method further includes controlling a temperature of the blown air from at least one of a cooling element and a heating element.

In accordance with another embodiment of the present invention, a sleep surface insert system for positioning under an infant on a sleep surface is provided. The sleep surface insert system includes an insert and a blower and, further includes a monitoring system. The insert is configured to be placed on the sleep surface and includes a substantially flat configuration. Further, the insert includes a top liner having an exterior surface and a bottom liner, the top liner and bottom liner defining at least one hollow space therebetween. The top liner defines multiple pores extending between the at least one hollow space and the exterior surface. The blower is configured to provide air flow into the at least one hollow space defined in the insert. The air flow is configured to flow into the insert and out of the multiple pores. The monitoring system is coupled to the insert and is configured to monitor at least one of heart rate and respiration of the infant.

In another embodiment, the sleep surface insert system also includes a controller and a sensor configured to control a temperature of the air being blown through the insert. In another embodiment, the sleep surface insert system includes a filter configured to filter the air being blown through the insert.

In another embodiment, the monitoring system includes a piezoelectric film. In still another embodiment, the monitoring system includes a conductive polymer. In yet another embodiment, the monitoring system includes a pressure sensor. In another embodiment, the monitoring system includes closely spaced conductors. In another embodiment, the monitoring system includes a surface pressure sensor.

In one embodiment, the at least one hollow space includes a first hollow space and as second hollow space defined between the top liner and the bottom liner. In another embodiment, the sleep surface insert system also includes an actuator positioned between the blower and the insert that is configured to direct the air flow between the first hollow space and the second hollow space in an alternating manner. In still another embodiment, the multiple pores include first multiple pores and second multiple pores corresponding with the first hollow space and the second hollow space, respectively.

In another embodiment, the insert is sized and configured to correspond with a bed mattress. In another embodiment, the insert is sized and configured to correspond with a head pillow.

In accordance with another embodiment of the present invention, an air flow insert system for positioning under an infant on a sleep surface is provided. The sleep surface insert system includes an insert and a blower. The insert is configured to be positioned over the sleep surface such that the insert includes a first portion and a second portion coupled together. The first portion is configured to extend generally horizontally over the sleep surface. The second portion extends generally transverse relative to the first portion from a periphery of the first portion such that the second portion is configured to extend upward from the first portion to provide a wall extending around the periphery of the first portion. The first portion includes a top liner and a bottom liner such that the top liner includes first portion apertures defined therein. The second portion includes an inner liner and an outer liner such that the inner liner includes second portion apertures defined therein. The insert includes at least one chamber defined within the first portion and the second portion such that the first portion apertures and the second portion apertures correspond with the at least one chamber defined in the first portion and the second portion of the insert. The blower is configured to provide air flow into the at least one chamber defined in the insert. The air flow is configured to flow into the insert and out of the first portion apertures and the second portion apertures so as to provide air flow from the first portion apertures in a generally vertical direction and to provide air flow from the second portion apertures in a generally horizontal direction to flow above the first portion.

In one embodiment, the insert includes a first chamber and a second chamber defined therein such that the first and second chambers receive the air flow in an alternating manner. In another embodiment, the air flow insert system further includes an actuator configured to alternate inflation of the insert between the first and second chambers. In still another embodiment, the insert includes a single chamber configured to receive air and provide air flow through the first and second portion apertures. In yet another embodiment, the air flow insert system further includes a sensor, a controller and a thermal element configured to control a temperature of the air flow moving into the insert. In another embodiment, the air flow insert system further includes a filter configured to filter the air flow moving into the insert.

In accordance with another embodiment of the present invention, an air flow insert system for positioning over or adjacent a sleep surface of an infant is provided. The sleep surface insert system includes an insert and a blower. The insert is configured to at least partially surround the sleep surface of an infant. The insert includes an elongated dimension and a height dimension such that the elongated dimension is configured to extend along the sleep surface and the height dimension is configured to extend upward from the sleep surface. The insert includes an inner liner and an outer liner. The inner liner and the outer liner is configured to extend generally vertically between a bottom end and a top end of the insert to define the height dimension. The inner liner and the outer liner defines at least one chamber therebetween and the inner liner defines multiple apertures extending therethrough. The blower is configured to provide air flow into the at least one chamber defined in the insert. The air flow is configured to flow into the insert and out of the insert from the multiple apertures defined in the generally vertically extending inner liner so that the air flow from the apertures flows in a generally horizontal direction.

In one embodiment, the air flow insert system further includes a sensor, a controller and a thermal element configured to control a temperature of the air flow moving into the insert. Also, in another embodiment, the air flow insert system further includes a filter configured to filter the air flow moving into the insert.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 5 is a perspective view of another embodiment of a sleep surface insert system, depicting an insert having horizontal portion and vertical portion thereof, according to the present invention;

FIG. 5A is a cross-sectional view of the insert taken along section 5A of FIG. 5, according to another embodiment of the present invention;

FIG. 5B is an enlarged view of region 5B of the insert of FIG. 5, according to another embodiment of the present invention;

FIG. 5C is an enlarged view of another embodiment of region 5B of the insert of FIG. 5, according to the present invention;

FIG. 6 is a cross-sectional view of another embodiment of the sleep surface insert system of FIG. 5, depicting a removable pad liner to be positioned in the insert, according to the present invention;

DETAILED DESCRIPTION OF THE INVENTION

Figures 1, 1A:
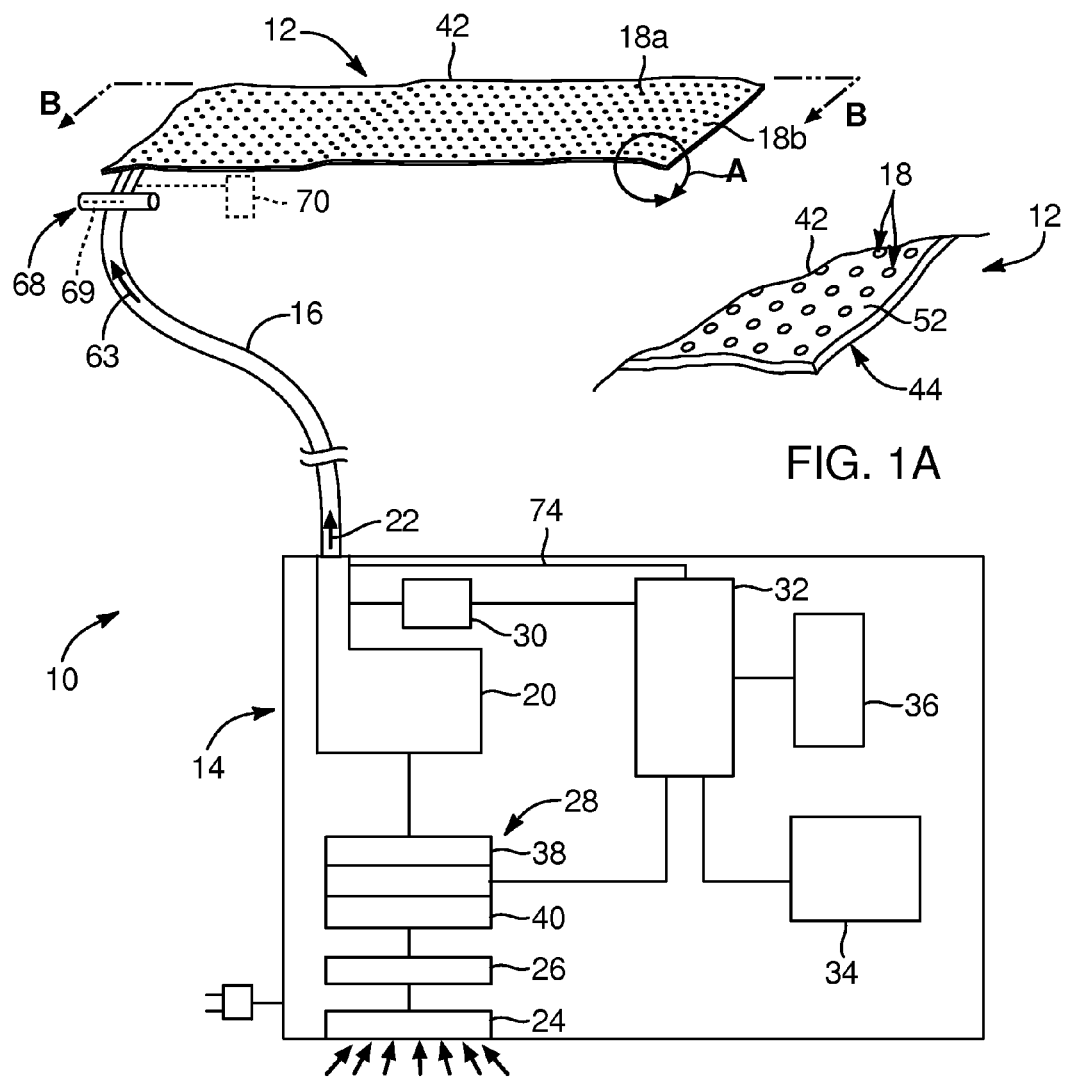
FIG. 1 is a partial schematic view of a sleep surface insert system, depicting an insert and a blower system, according to an embodiment of the present invention.
FIG. 1A is an enlarged view of region A of the insert, of FIG. 1, according to one embodiment of the present invention.

Referring to FIG. 1, a sleep surface insert system 10 configured to, for example, substantially eliminate the conditions leading to SIDS is provided. As will be apparent to one of ordinary skill in the art, the insert system may be employed for other purposes, as set forth herein in the various embodiments. In one embodiment, such a sleep surface insert system 10 may provide oxygen to an infant (not shown) positioned over a portion of the system 10 while also jostling or slightly rocking the infant lying thereon. In another embodiment, the sleep surface insert system 10 may monitor the heart rate and/or respiration of the infant while providing oxygen to an infant positioned over a portion of the system 10. For example, the sleep surface insert system 10 may include an insert 12 and a blower system 14 with a conduit 16 extending therebetween. The blower system 14 may be configured to direct air flow through the conduit 16 and into the insert 12 to inflate portions of the insert 12, in an alternating manner, to slightly rock or jostle an infant positioned over the insert 12 while also flowing oxygen through multiple pores 18 in the insert, thereby, ensuring ample oxygen is present for the infant. In this manner, such movement of the infant may ensure the elimination of potential air pockets of carbon dioxide forming while also providing oxygen through the multiple pores 18. Further, the insert 12 may be a substantially flat configuration such that it may be positioned over a mattress (not shown) or other suitable sleeping surface. Further, the insert 12 may include a comfort liner (not shown) that may be slipped over the insert 12 as well as removed to wash when necessary.

The blower system 14 may include a blower 20 configured to blow air, as indicated by arrow 22, into the insert 12 via the conduit 16. Further, the blower system 14 may include an air intake 24, a filter 26, a thermal element 28, one or more sensors 30, a controller 32, a display 34, and a manual control 36. The blower 20 may pull air from the air intake 24 toward the blower 20 and then push the air through the conduit 16 and into the insert 12. In addition, the filter 26 may be provided between the conduit 16 and the air intake 24 and, more particularly, the filter 26 may be positioned between the air intake 24 and the blower 20. The thermal element 28 may also be positioned between the air intake 24 and the conduit 16. The controller 32 may be coupled to the one or more sensors 30 and the thermal element 28 and, further, the manual control 36. Also, the controller 32 may be coupled to the display 34. The one or more sensors 30 may be positioned along an air flow path to sense air temperature and/or air pressure.

In one embodiment, air temperature of the sleep surface insert system 10 may be controlled. For example, the air temperature may be controlled by manually setting a desired temperature for an infant via the manual control 36. The one or more sensors 30 may sense the actual temperature of the air and then relay the actual temperature to the controller 32. The controller 32 may then control the thermal element 28, positioned in an air flow path, to modify the air temperature from the actual air temperature to the desired air temperature.

In one embodiment, the thermal element 28 may be positioned in the air flow path between the air intake 24 and the blower 20. In another embodiment, the thermal element 28 may be positioned in the air flow path between the blower 20 and the conduit 16 or, otherwise said, an external portion of the conduit 16. In one embodiment, the thermal element 28 may include a heating element 38. In another embodiment, the thermal element 28 may include a cooling element 40. In still another embodiment, the thermal element 28 may include both a heating element 38 and a cooling element 40. Such a heating element 38 and cooling element 40 may be directly coupled adjacent to each other or separate from each other. The heating element 38 may be a coil or the like or any other suitable heating element known in the art, such as a peltier element employed as a heating element. The cooling element 40 may be a peltier element or any other suitable cooling element known in the art.

Figure 2:
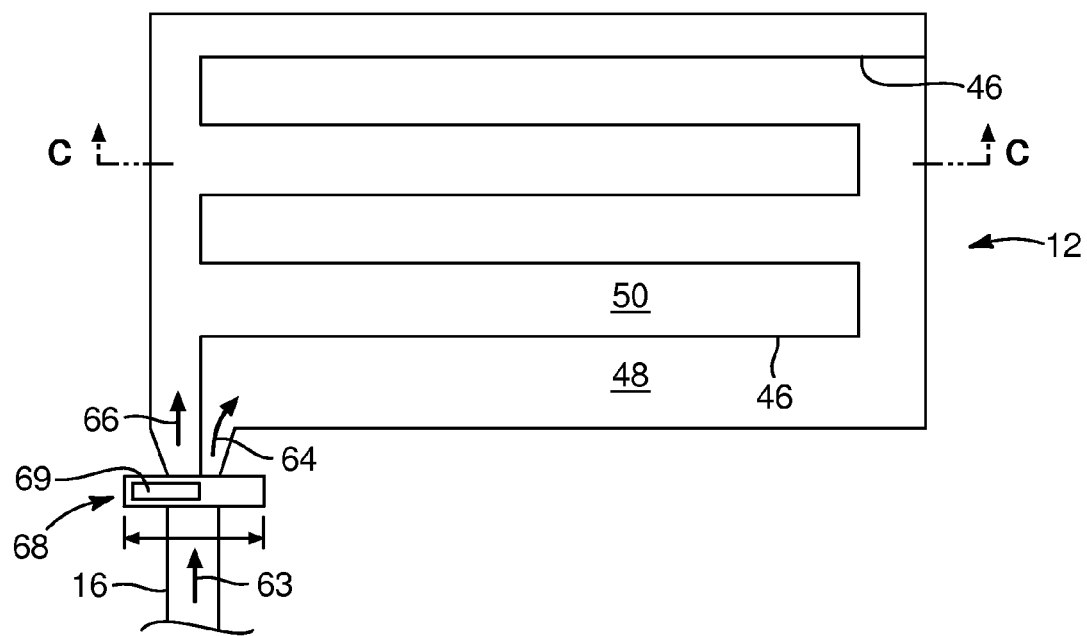
FIG. 2 is a cross-sectional view of the insert taken along section B of FIG. 1, according to another embodiment of the present invention.
Figure 3:
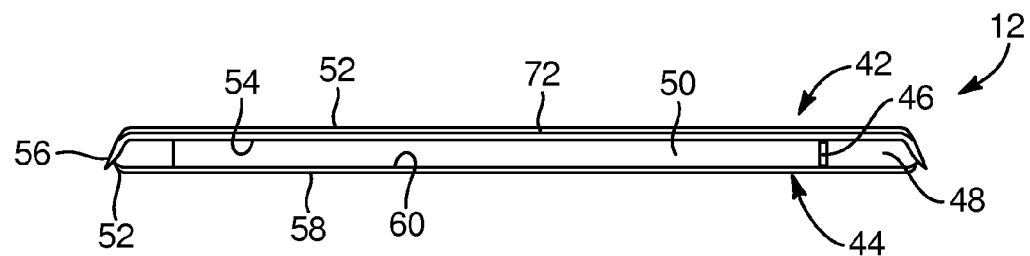
FIG. 3 is a cross-sectional view of the insert taken along section C of FIG. 2, according to another embodiment of the present invention.

With respect to FIGS. 1, 2, and 3, the insert 12 may include a top liner 42 and a bottom liner 44 with one or more hollow spaces defined therebetween. In one embodiment, a single hollow space (not shown) may be defined between the top liner 42 and the bottom liner 44. In another embodiment, the insert 12 may include a lateral wall 42 extending transverse or substantially orthogonal between and relative to the top liner 42 and the bottom liner 44. Such lateral wall 46 may separate and define a first hollow space 48 and a second hollow space 50 between the top liner 42 and the bottom liner 44. In another embodiment, the lateral wall 46 may define multiple hollow spaces between the top liner 42 and the bottom liner 44, for example, three or more hollow spaces.

With reference to FIGS. 1, 1A, and 3, the top liner 42 may include an outer surface 52, or exterior surface, and an inner surface 54 with a periphery defining an edge 56 of the fop liner 42. The bottom liner 44 may include a bottom surface 58 and an inner surface 60 defined by a bottom liner periphery 62. The top liner 42 may be sized and configured to substantially correspond with dimensions of the bottom liner 44 such that their respective peripheries may be coupled together or, rather, the portion adjacent their respective peripheries may be coupled together.

Further, the top liner 42 may include multiple pores 18 extending between the outer surface 52 and the inner surface 54 configured to facilitate air flow therethrough. Such multiple pores 18 may be in the form of holes, as depicted in FIG. 1A, formed through the top liner 42 extending between the first and second hollow spaced 48, 50 and the outer surface 52 of the top liner 42. The multiple pores 18 may include first multiple pores 18a and second multiple pores 18b that may be distinguished by corresponding with the respective first and second hollow spaces 48, 50 defined in the insert 12.

The multiple pores 18 may be in the form of an array such that the multiple pores 18 may be sized, positioned and/or spaced in a predetermined manner. In this embodiment, the top liner 42 may include a polymeric material in a sheet like form. In another embodiment, the multiple pores 18 may be randomly sized, positioned and/or spaced. In this embodiment, the top liner 42 may be formed from a weaved material or the like such that the multiple pores 18 are inherent to the gaps or spaces formed in the weaved material. Such a top liner 42 may be formed from a synthetic material, such as a polymeric material, or the top liner may be formed from a natural material, such as a cotton, or various combinations or blends thereof or any other suitable material that is safe and provides multiple pores 18 so as to facilitate air through the multiple pores 18, as known by one of ordinary skill in the art. The bottom liner 44 may be formed of a solid sheet like material, without pores, so as not to facilitate air to flow therethrough. In another embodiment, the bottom liner 44 may be formed to include pores, similar to the top liner 42. Further, in one embodiment, the top liner 42 and the bottom liner 44 may be coupled together via heat pressing, sewing or any other known or suitable method of coupling. In another embodiment, the top liner 42 and the bottom liner 44 may be formed of a continuous, unitary, and/or seamless material.

Referring now to FIGS. 1 and 2, the conduit 16 may be coupled between the blower 20 or blower system 14 and the insert 12. Further, the conduit 16 may branch from a single flow path 63 to a first flow path 64 and a second flow path 66, the first flow 64 path configured to correspond with the first hollow space 48 and the second flow path 66 to correspond wife the second hollow space 50 defined in the insert 12. Further, the conduit 16 may include an actuator 68 coupled thereto. The actuator 68 may be sized and configured to alternate air flow in the conduit 16 between the first flow path 64 and the second flow path 66, thereby, alternating air flow between the first hollow space 48 and the second hollow space 50 defined in the insert 12. With this arrangement, the actuator 68 alternates air flow between the first hollow space 48 and the second hollow space 50 defined in the insert 12, thereby, facilitating movement of the insert 12 so that an infant lying over the insert 12 may continuously be rocked or lightly jostled to, for example, gently stimulate the infant's nervous system to encourage proper function and reaction to diminished oxygen or, rather, excessive carbon dioxide. In addition, air flowing through the multiple pores 18 further ensures ample oxygen for the infant that may be lying face down on a sleep surface.

The actuator 68 may be a timed actuator in the form of a solenoid 69. For example, the actuator 68 may actuate at a frequency. Such a frequency may be manually modified to control the cycle by which air flow is directed into the first and second hollow spaces 48, 50 for alternately inflating different portions of the insert 12. The actuator 68 may also include a pressure sensor 70 that may be configured to actuate upon sensing a predetermined air pressure within the first flow path 64 and the second flow path 66 and, thus, the air pressure within the respective first and second hollow spaces 48, 50 defined in the insert 12. In another embodiment, the actuator 68 may be a bladder controlled diverter (not shown). Such a bladder controlled diverter may be sized and configured to inherently and mechanically actuate between a first position and a second position upon the respective first hollow space 48 and the second hollow space 50 of the insert 12 or bladder inflating to a predetermined air pressure. In other words, the bladder controlled diverter may automatically actuate between the first and second positions upon portions of the bladder, i.e., first and second hollow spaces 48, 50 in the insert, reaching predetermined inflation levels.

Referring now to FIGS. 1 and 3, in another embodiment, as previously set forth, the sleep surface insert system 10 may monitor various physiological parameters of the infant (or person), such as the heart rate, and/or respiration of an infant while also providing oxygen to the infant positioned over the insert 12 of the system 10. Other physiological parameters may include movement, moisture, such as bed wetting, and a temperature of the infant. Such monitoring may be employed with one or more sensors, such as, a pressure sensor, conductive polymer (resistance inflections), closely separated conductors, i.e., capacitance/resistance inflections. For example, the insert 12 may include a sensor in the form of a piezoelectric film 72. Such film may include lines or wires 74 extending from the insert 12 along the conduit 16 to be coupled to, for example, the controller, which may then provide information at the display 34. The piezoelectric film 72 may be configured to sense slight force, movement, thermal, and/or pressure changes to facilitate monitoring an infant's heart rate and respiration. The controller 32 may also be configured to provide an alarm (not shown) if significant changes in the heart rate and respiration are sensed to ensure potential issues with an infant are alleviated. Such alarm may be set-off from, for example, the system itself or transmitted remotely to a location of the infant's parents.

Figure 4:
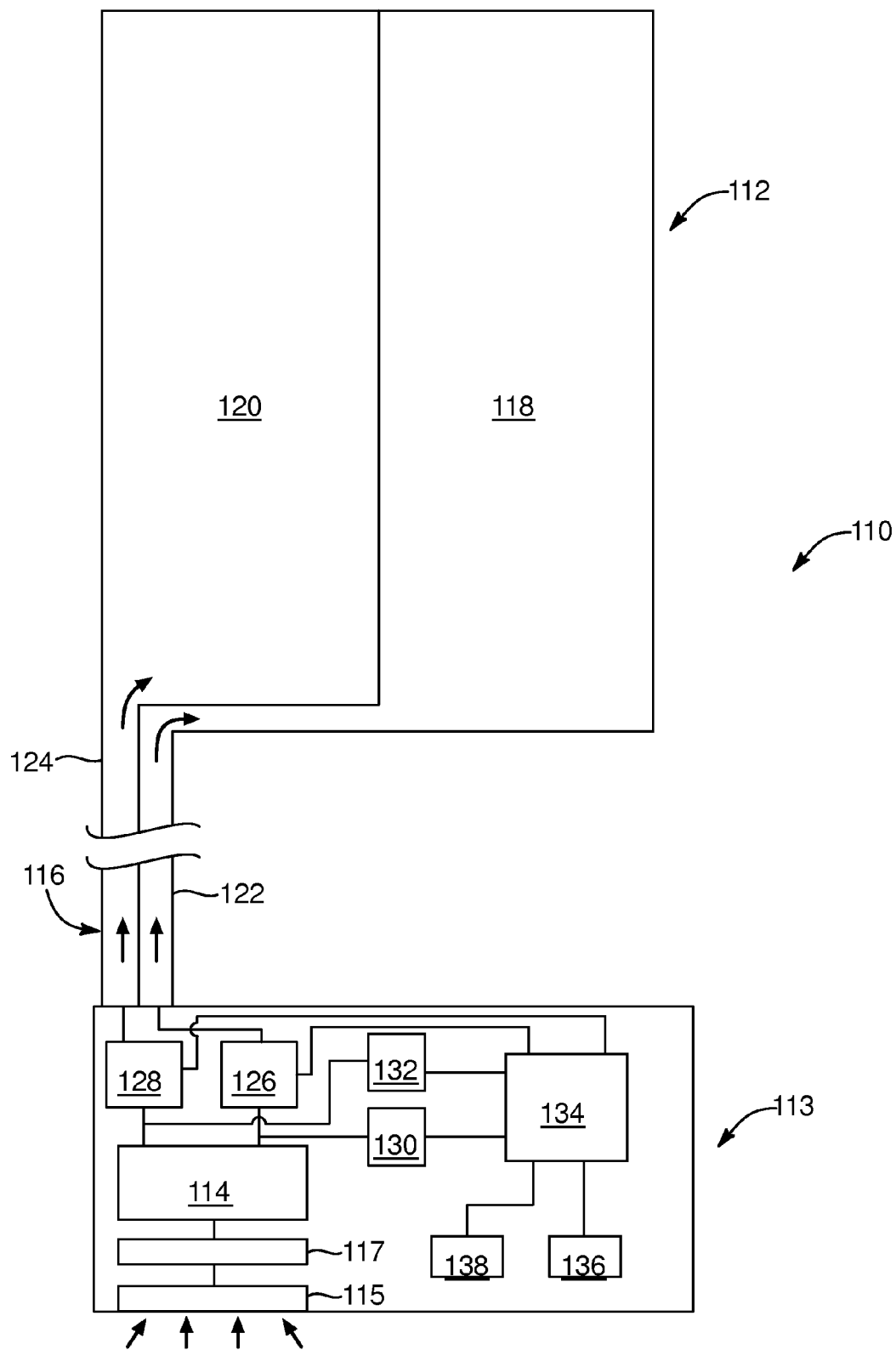
FIG. 4 is another embodiment of a sleep surface insert system, according to another embodiment of the present invention.

Now referring to FIG. 4, a sleep surface insert system 110 of another embodiment is provided. This system is similar in many respects to the previous embodiment of FIG. 1, however, the sleep surface insert system 110 of this embodiment may not include an actuator to alternate air flow between two hollow spaces defined in an insert. Rather, in this embodiment, one primary function of the sleep surface insert system 110 may be configured to control temperature of air being blown through pores (not shown) defined in the top liner of the insert 112.

For example, the sleep surface insert system 110 may include an insert 112 and a blower system 113 with conduit 116 extending therebetween. The blower system 113 may include an air intake 115 and filter 117, as set forth in the previous embodiment. In one embodiment, the insert 112 may include a first hollow space 118 and a second hollow space 120 defined in the insert 112 between a top liner and a bottom liner (not shown). Each hollow space defined in the insert 112 may include its own conduit extending from the insert to the blower system, namely, a first conduit 122 and a second conduit 124. The first and second conduits 122, 124 may be in the form of a single elongated flexible member, but include respective first and second lumens to channel air flow to the respective first and second hollow spaces 118, 120 defined in the insert 112. The blower system 113 may include a single blower 114 or two blowers dedicated to the respective first and second conduits 122, 124. Further, each air flow path for the first and second conduits 122, 124 may include a first thermal element 126 and a second thermal element 128, respectively. Each thermal element may each include a cooling element and a heating element. The blower system 113 may also include the other components necessary to control a temperature of the air being blown toward the insert 112. For example, the blower system 113 may include a first sensor 130 and a second sensor 132 configured to sense the actual temperature being blown and a controller 134 coupled to the first and second thermal elements 126, 128 to modify the actual temperature to a desired temperature as manually set via a first and second manual control 136, 138. With this arrangement, the sleep surface insert system 110 may be configured to control the temperature over two sleep surface portions of the insert 112 such that the defined first and second hollow spaces 118, 120 correspond with sleep surface portions typical for two persons lying next to each other. Such a system 110 may be desirable for couples who desire different temperatures for their respective sleep portions. Further, the insert 112 may be sized and configured for single person users such that the insert 112 may include a single hollow space with a corresponding single thermal element and sensor in the blower system.

In one embodiment, the insert 112 may be sized and configured to be positioned over a pillow or within a pillow cover.

In another embodiment, the insert 112 may be sized and configured to act as a pillow itself while employing one or various combinations of the functions described herein with the sleep surface insert system 110, such as monitoring temperature and temperature control, air filtering, inflation of one hollow space defined in an insert, and alternating (or sequencing) inflation of two or more hollow spaced defined within an insert. In still another embodiment, by employing various functions described herein, the sleep surface insert system 10, 110 may be employed to monitor not only infants, but to monitor sleep disorders, such as sleep apnea or any other suitable sleep disorder. In another embodiment, the insert 10 described in FIG. 1 may be sized to act with or as a pillow and include a single chamber (or multiple chambers) defined in the insert. Such insert of this embodiment may include various controls and/or sensors to assist in monitoring, for example, sleep apnea, asthma, or a temperature of the person laying on the pillow with the insert, and utilize one or more of the functions described herein, such as filtering the air flowing into the insert and controlling the temperature of the air.

Now referring to FIG. 5, another embodiment of a sleep surface insert system 200 is provided. In this embodiment, the sleep surface insert system 200 may be similar to the embodiment described in FIGS. 1 through 3, but may also include transversely or vertically extending side walls, as depicted, that provide a wall or barrier to the sleep surface insert system 200. The sleep surface insert system 200 may be sized and configured to be positioned over a crib-sized mattress (not shown) or positioned over any sleep surface so as to provide air flow through apertures 202 or pores, similar to that previously described. The vertical side walls also provide cushioning and a barrier for a baby's head and body from the rigid bars or walls of, for example, an infant's crib.

With respect to FIGS. 5, 5A, and 5B, the sleep surface insert system may include an insert 204, a blower system 14 (FIG. 1), and conduit 206 extending between the insert 204 and the Mower system 14. The insert 204 may include a first portion or horizontal portion 208 and a second portion or vertical portion 210, the vertical portion 210 extending transverse or upward from a periphery of the horizontal portion 208 so as to provide the wall or barrier. It is noted that the vertical portion 210 is not necessarily precisely vertical relative to a horizontal plane, but rather, may include a vertical component that is transverse relative to the horizontal portion of the insert 204 to provide the wall or barrier.

In one embodiment, for example, the horizontal portion 208 may be rectangular and substantially flat such that the vertical portion 210 may include first and second facing vertical sides 212, 214 and third and fourth facing vertical sides 216, 218, each of which may extend upward and transverse relative to the horizontal portion 208. In one embodiment, the various sides of the vertical portion 210 may extend generally or substantially vertical relative to the horizontal portion 208 with the transition from the horizontal portion 208 to the vertical portion 210 being arcuate. The first vertical side 212 may be contiguous with the third and fourth vertical sides 216, 218. Likewise, the second vertical side 214 may be contiguous with the third and fourth vertical sides 216, 218. The periphery of the horizontal portion 208 of the insert 204 may include other shapes, such as oval or any other suitable shape, such that the vertical portion extends upward from the periphery of the horizontal portion to provide the wall or barrier for an infant.

The horizontal portion 208 may include a top liner 220 and a bottom liner 222 that define first and second hollow spaces 224, 226 or chambers therebetween, similar to the insert 12 depicted in FIGS. 1 through 3, but the first and second hollow spaces 224, 226 may continue Into the vertical portion 210 of the insert 204. The vertical portion 210 may include an inner liner 228 and an outer liner 230 also defining the first and second hollow spaces 224, 226 or chambers. The inner liner 228 may be contiguous with the top liner 220. Likewise, the bottom liner 222 may be contiguous with the outer finer 230 of the insert.

The top liner 220 of the horizontal portion 208 and the inner liner 228 of the vertical portion 210 may include apertures 202 defined therein. For example, the apertures 202 defined in the top liner 220 and the inner liner 228 may each include first apertures 202*a* and second apertures 202*b*, the first apertures 202*a* corresponding with the first hollow space 224 and the second apertures 202*b* corresponding with the second hollow space 226. Similar to the horizontal portion 208, each of the vertical sides of the vertical portion 210 may each include one of the first and second hollow spaces 224, 226, or both. Further, the first and second hollow spaces 224, 226 may be separated by one or more impermeable lateral connections 240. Such lateral connections 240 assist in maintaining the top and bottom liners 220, 222 of the horizontal portion 208 in a generally parallel configuration. Likewise, the lateral connections 240 assist in maintaining the inner liner 228 generally parallel relative to the outer liner 230 of the vertical portion 210. Further, the lateral connections 240 may serve to separate the first and second hollow spaces 224, 226 in a discrete and distinct manner.

The blower system 14 (FIG. 1) may provide air pressure or air flow 236 into each of the first and second hollow spaces 224, 226 such that air flow 236 moves outward from the apertures 202 associated with each of the first and second hollow spaces 224, 226. As depicted in FIG. 5B, the air flow 236 moves generally in a horizontal direction (as depicted with horizontal direction arrows) from the vertical portion 210 of the insert 204 and generally in a vertical direction (as depicted with vertical direction arrows) from the horizontal portion 208 of the insert 204. It is noted that the vertical portion 210 may not extend precisely vertical relative to the horizontal portion 208, but rather, may extend upward and transverse relative to the horizontal portion 208 so as to provide a wall or barrier. As such, the apertures 202 in the vertical portion 210 may provide air flow in a general horizontal direction such that the air flow 236 flowing from the vertical portion 210 flows transverse relative the air flow 236 flowing from the horizontal portion 208. In this manner, the vertical portion 210 provides the wall or barrier and, further provides, air flow 236 from the vertical portion 210 that flows transverse relative to the air flow 236 from the horizontal portion 208, but not necessarily air flow that is precisely perpendicular relative to each other.

Further, the blower system 14 may provide air flow 236 in an alternating manner via an actuator 68 (FIG. 1) between the two chambers or first and second hollow spaces 224, 226 defined in the insert 204 so as to rock or jostle an infant on the insert 204 as well as provide substantially continuous air flow 236 to the infant regardless of the position of the infant on the insert 204. In addition, in the event an infant's face becomes positioned against a vertical portion 210 of the insert 204, the infant is provided additional air flow 236 through the apertures 202 defined in the inner liner 228 of the vertical portion 210 as well as the vertical portion 210 serving as a soft pad for the infant's head or body.

As in the previous embodiment (depicted in FIGS. 1 through 3), the blower system 14 and conduit 206 of this embodiment may include pressure and heart rate sensors as well as a temperature control to manage the air flow temperature for the infant. The conduit may also include, for example, two air flow channels (as depicted by broken line 238) for blowing air therethrough as well as an actuator for alternating air flow between the two air flow channels that funnel air into the first and second hollow spaces 224, 226, as well as any of the other structural and functional components described and depicted in FIGS. 1 through 3. Further, the insert 204, including the horizontal and vertical portions 208, 210, may be formed of a similar material as that described in the embodiment described in FIG. 1, or any other suitable materials as known to one of ordinary skill in the art.

In another embodiment, the conduit 206 may be optional such that the blower system 14 is directly coupled to the insert. The embodiment with an optional conduit may be implemented in any of the embodiments described herein, as known to one of ordinary skill in the art.

As depicted in FIG. 5C, another embodiment of a sleep surface insert system 201 is provided. This embodiment is substantially similar to that described and depicted in FIGS. 5 and 5A, except in this embodiment the insert 205 may include a single air-flow chamber 207 defined therein. The insert may include lateral connections 209 extending between the top liner 211 and the bottom liner 213 of the horizontal portion 215 as well as the inner liner 217 and the outer liner 219 of the vertical portion 221. Such lateral connections 209 may also extend between the liners to define channels of the single chamber 207. As in the previous embodiment, the inner liner 217 of the vertical portion 221 may define apertures 223 as well as the top liner 211 of the horizontal portion 215 may define apertures 223. In this embodiment, each of the apertures 223 communicate or are associated with the single chamber 207 to facilitate air flow from the blower system 14 (FIG. 1) such that apertures 223 in the horizontal portion 215 provide air flow upward in a general vertical direction, as depicted by arrows 225, and the apertures 223 defined in the vertical portion 221 of the insert may provide air flow in a general horizontal direction, as depicted by arrows 227.

The blower system 14 of this embodiment may be similar to that described and depicted in FIGS. 1 and 2, including the structural and functional components described therewith. Further, since the insert 205 of this embodiment has a single chamber, any conduit employed may only define a single channel therein and the sleep surface insert system 201 may not require an actuator, as in other embodiments described herein.

With respect to FIG. 6, another embodiment of the sleep surface insert system 200 is provided. In this embodiment, the insert 204 may be similar to that provided in the previous embodiment, but the system 200 may include a removable pad liner 250 for positioning and resting over the horizontal portion 208 and within the walls of the vertical portion 210 of the insert 204. The pad liner 250 may include a cushion portion 252 and an outer liner 254. The cushion portion 252 may be a foam material, such as an open cell foam or reticulated foam or similar material that facilitates air flow therethrough. The outer liner 254 may be a fabric or the like, such as a knitted or weaved material, that also readily facilitates air flow therethrough. The outer liner 254 may be coupled to an upper surface of the cushion portion 252 or be positioned around the cushion portion 252 in a sleeve-like manner. Such pad liner 250 may be removed from the insert 204 for purposes of cleaning such that the whole pad liner 250 may be washed or the outer liner 254 may be removed from the cushion portion 252 for cleaning the outer liner 254 separate from the cushion portion 252. With this arrangement, the pad liner 250 may be made of a material that provides additional comfort to an infant and also allows the flow of air from the insert 204 and through the pad liner 250 while also being removable for long term sanitary purposes.

Figure 7:
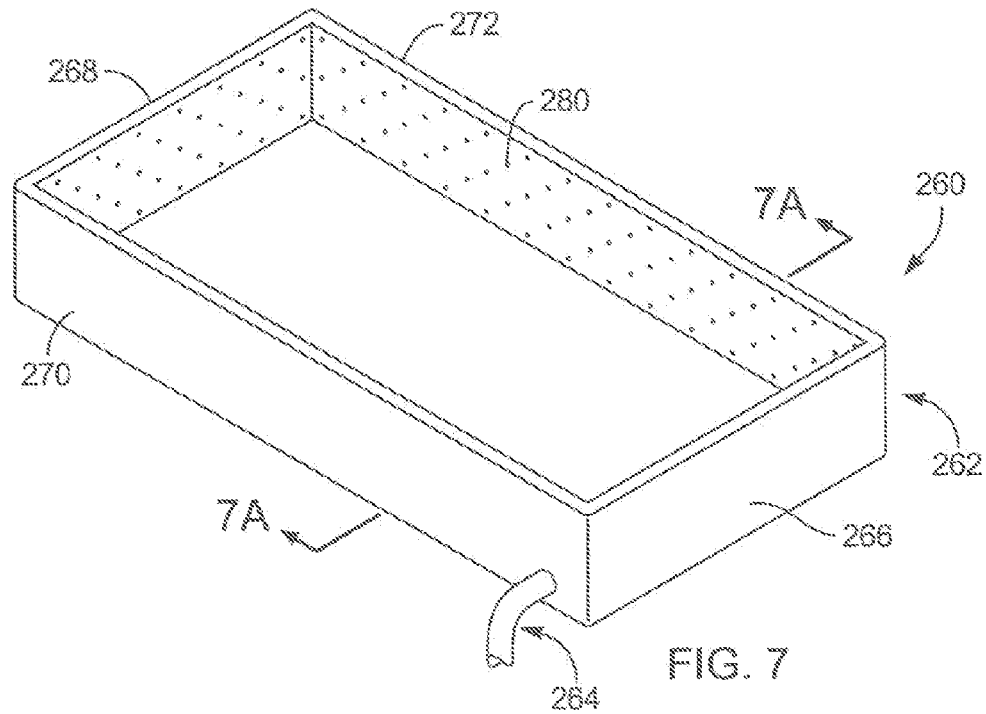
FIG. 7 is a perspective view of another embodiment of an air flow insert system, depicting an insert including a vertical portion, according to the present invention.
Figure 7A:
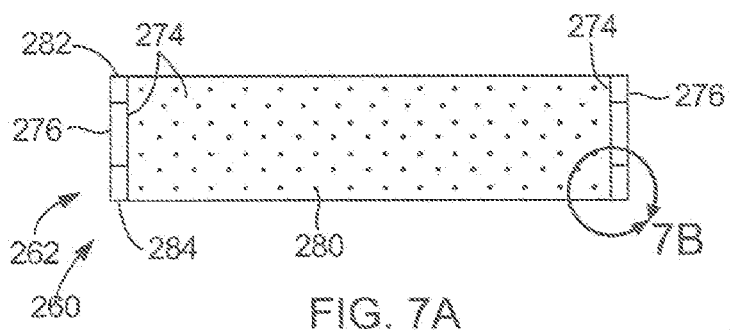
FIG. 7A is a cross-sectional view of the insert taken along section 7A of FIG. 7, according to another embodiment of the present invention.
Figure 7B:
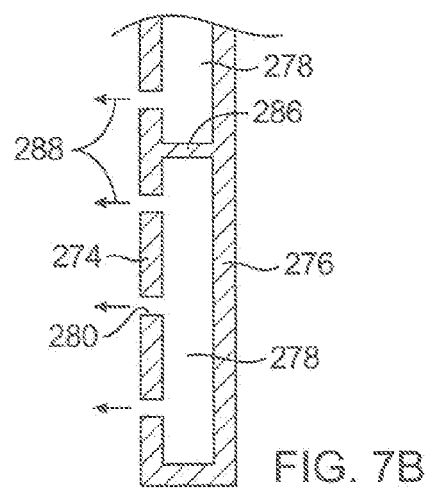
FIG. 7B is an enlarged, view of region 7B of the insert of FIG. 7, according to another embodiment of the present invention.

With reference to FIGS. 7, 7A, and 7B, another embodiment of an air flow system 260 is provided. The air flow system 260 is similar to the embodiment described and depicted in FIG. 5, except the air flow system 260 may not include air chambers defined and extending along a horizontal portion, but rather, includes air chambers defined and extending in a vertical portion 262 as the insert. The vertical portion 262 of the air flow system 260 of this embodiment may be sized and configured to act as a bumper pad in, for example, an infant's crib. The air flow system 260 may include the vertical portion 262, a blower system 14 (FIG. 1), and a conduit 264, the conduit 264 extending between the vertical portion 262 and the blower system 14. Such a blower system 14 and conduit 264 may include all or some of the structural and functional components described relative to the embodiment of FIG. 1.

The vertical portion 262 may include first and second facing vertical portions 266, 268 and third and fourth facing vertical portions 270, 272, each of which may border an interior side portion of an infant's crib (not shown). For example, each of the first, second, third and fourth vertical portions 266, 268, 270, 272 may be elongated to extend along one of the interior side portions of the crib as well as each extend with a vertical component to provide padding for an infant within the crib in the event, for example, the baby rolls over against one of the vertical portions. Each vertical portion may include an inner liner 274 and an outer liner 276 with one or more chambers or hollow spaces 278 defined therebetween.

The inner liner 274 may include perforations or apertures 280 and the outer liner 276 may be impermeable. Further, the inner liner 274 and outer liner 276 may be coupled together along a top end 282 and a bottom end 284 as well as include lateral connections 286 at various points between the top and bottom ends 282, 284 so that each vertical portion maintains a generally rectangular cross-sectional shape. As in previous embodiments, the inner liner 274 and the outer liner 276 may be formed of a polymeric material, or fabric, or a combination thereof. The lateral connections 286 and coupling along the top and bottom ends 282, 284 may be employed by thermal bonding or sewing or any other suitable means of coupling. With this arrangement, air flow 288 may be provided via the conduit 264 to the one or more hollow spaces 278 or chambers so as to provide air flow 288 from a vertically extending wall or inner liner 274 and through the apertures 280 such that the air flow 288 exits the vertically extending wall or inner liner 274 in a generally horizontal direction, as depicted with arrows in FIG. 7B. In this manner, the vertical portions 262 provide padding for an infant as well as provide air flow 288 to an infant if the infant's face moves against the vertical portion 262 of the air flow system 260.

The conduit 264 may include one or two flow paths depending on the number of chambers defined in the vertical portion of the air flow system 260. For example, in the case of a single chamber or hollow space defined in the vertical portion 262, the conduit 264 may include a single flow path through which air may be blown by the blower system 14 (FIG. 1). As in previous embodiments, in the case of two chambers or hollow spaces defined in the vertical portion 262, the conduit 264 may include two flow paths for tunneling air to the two chambers and also may include the actuator to alternate inflation of the chambers.

While the invention may be susceptible to various modifications and alternative forms, specific embodiments have been shown by way of example in the drawings and have been described in detail herein. Further, the structural features of any one embodiment disclosed herein may be combined or replaced by any one of the structural features of another embodiment set forth herein. As such, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A sleep surface insert system for positioning under an infant on a sleep surface, the sleep surface insert system comprising:
    a removable insert configured to be placed on the sleep surface, the removable insert having a substantially flat configuration with a top liner having an exterior surface and a bottom liner, the top liner and bottom liner defining a first hollow space and a second hollow space therebetween, the top liner including first multiple pores and second multiple pores defined therein, the first multiple pores extending between the first hollow space and the exterior surface of the top liner and the second multiple pores extending between the second hollow space and the exterior surface of the top liner;
    a blower configured to provide air flow into the first hollow space and the second hollow space defined in the removable insert, the air flow configured to flow into the removable insert and out of at least one of the first multiple pores and the second multiple pores;
    an actuator configured to alternate inflation of the removable insert between the first hollow space and the second hollow space defined therein; and
    a sensor, a controller and a thermal element each operatively coupled to the blower and configured to control a temperature of the air being blown through the removable insert.

2. The sleep surface insert system of claim 1, wherein the actuator comprises a solenoid.

3. The sleep surface insert system of claim 1, wherein the actuator is configured to actuate with a predetermined frequency.

4. The sleep surface insert system of claim 1, wherein the actuator comprises a sensor, the actuator being configured to actuate upon sensing a predetermined pressure.

5. The sleep surface insert system of claim 1, further comprising a filter configured to filter the air being blown through the removable insert.

6. A method of substantially eliminating risk factors which lead to sudden infant death syndrome, the method comprising:
    positioning a removable insert on a sleep surface such that the removable insert includes a top liner and a bottom liner that defines a first hollow space and a second hollow space therebetween, the top liner including first multiple pores and second multiple pores defined therein that correspond with the first and second hollow spaces defined in the removable insert, respectively;
    blowing air into the removable insert and through the first multiple pores and the second multiple pores such that the air is directed in an alternating manner between the first hollow space and the second hollow space to inflate the removable insert between the first hollow space and the second hollow space of the removable insert; and
    controlling a temperature of the blown air with at least one of a cooling element and a heating element.

7. The method according to claim 6, wherein the positioning comprises positioning the removable insert to be associated with at least one of a bed mattress and a head pillow.

8. The method according to claim 6, wherein the blowing comprises inflating portions of the removable insert corresponding with the first hollow space and the second hollow space to cause movement in a surface of the removable insert to jostle or rock an infant laying over the surface.

9. The method according to claim 6, further comprising monitoring at least one of the heart rate and respiration of the infant.

10. The method according to claim 6, wherein the blowing comprises filtering the air flowing into and out the first and second multiple pores of the removable insert for the infant.

11. The method according to claim 6, wherein the blowing comprises directing the air flow between the first hollow space and the second hollow space with an actuator.

12. The method according to claim 11, wherein the directing comprises alternating air flow between the first hollow space and the second hollow space by sensing a predetermined air pressure in the removable insert.

13. The sleep surface insert system of claim 1, wherein the removable insert is sized and configured to be associated with at least one of a bed mattress and a head pillow.

14. A sleep surface insert system for positioning under a person on a sleep surface, the sleep surface insert system comprising:
    a removable insert configured to be placed over the sleep surface, the removable insert having a substantially flat configuration with a top liner having an exterior surface and a bottom liner, the top liner and bottom liner defining at least one hollow space therebetween, the top liner defining multiple pores extending between the hollow space and the exterior surface;
    a blower configured to provide air flow into the at least one hollow space defined in the removable insert, the air flow configured to continuously flow into the removable insert and out of the multiple pores; and
    a monitoring system coupled to the removable insert and configured to monitor at least one of heart rate and respiration of the person.

15. The sleep surface insert system of claim 14, further comprising a controller and a sensor configured to control a temperature of the air being blown through the removable insert.

16. The sleep surface insert system of claim 14, further comprising a filter configured to filter the air being blown through the removable insert.

17. The sleep surface insert system of claim 14, wherein the monitoring system comprises at least one of a piezoelectric member, a conductive polymer, a pressure sensor, and spaced conductors.

18. The sleep surface insert system of claim 14, wherein the at least one hollow space comprises a first hollow space and a second hollow space defined between the top liner and the bottom liner.

19. The sleep surface insert system of claim 18, further comprising an actuator positioned between the blower and the removable insert configured to direct the air flow between the first hollow space and the second hollow space in an alternating manner.

20. The sleep surface insert system of claim 18, wherein the multiple pores comprises first multiple pores and second multiple pores corresponding with the first hollow space and the second hollow space, respectively.

21. The sleep surface insert system of claim 14, wherein the removable insert is sized and configured to be positioned over a bed mattress.

22. The sleep surface insert system of claim 14, wherein the removable insert is sized and configured to be associated with a head pillow.

* * * * *